United States Patent [19]

Taff et al.

[11] Patent Number: 4,940,058
[45] Date of Patent: Jul. 10, 1990

[54] CRYOGENIC REMOTE SENSING PHYSIOGRAPH

[76] Inventors: Barry E. Taff, 8665 Pickford St. #8, Los Angeles, Calif. 90035; Kenneth P. Stoller, 1319 Stratford Ave., South Pasadena, Calif. 91030

[21] Appl. No.: 205,085

[22] Filed: Jun. 10, 1988

Related U.S. Application Data

[63] Continuation-in-part of Ser. No. 871,925, Jun. 9, 1986, abandoned.

[51] Int. Cl.⁵ .............................................. A61B 5/00
[52] U.S. Cl. ................................. 128/653 R; 128/670; 128/671; 128/696; 128/716; 128/731; 128/733; 128/903; 343/893; 364/413.04
[58] Field of Search ............... 128/653, 670, 671, 731, 128/733, 716, 696, 903; 324/77 R, 77 A, 77 B, 77 G, ; 343/893; 364/413.04–413.06

[56] References Cited

U.S. PATENT DOCUMENTS

| | | | |
|---|---|---|---|
| 3,555,529 | 1/1971 | Brown et al. | 128/653 |
| 3,557,777 | 1/1971 | Cohen | 128/653 |
| 4,545,383 | 10/1985 | Toftness | 128/653 |

*Primary Examiner*—Ruth S. Smith
*Attorney, Agent, or Firm*—Philip D. Junkins

[57] ABSTRACT

Apparatus and method for remotely detecting super-low frequency (SLF) and extremely-low frequency (ELF) signals eminating from human subjects. The SLF/ELF signals are composed of various wavelengths and amplitudes which correspond to the subjects internal physiological processes. The apparatus includes: a supercooled multi-plate arrayed antenna for detecting the SLF/ELF signals; an analog signal conditioner unit adapted to filter out signals having a frequency of greater than 40 Hertz; and a digital signal processor unit adapted to perform Fast Fourier Transform and autocorrelation signal analyses for separating signal wavelengths and amplitudes which correspond to the internal physiological processes and represent EKG, EEG, EMG, EOG and respiration measurements.

9 Claims, 4 Drawing Sheets

ANALOG SIGNAL CONDITIONED SLF/ELF WAVEFORM

EKG WAVEFORM AFTER FFT/AUTOCORRELATION ANALYSIS AND D/A CONVERSION

EEG WAVEFORM AFTER FFT/AUTOCORRELATION ANALYSIS AND D/A CONVERSION

EEG WAVEFORM AFTER FFT/AUTOCORRELATION ANALYSIS AND D/A CONVERSION

RESPIRATION WAVEFORM AFTER FFT/AUTOCORRELATION ANALYSIS AND D/A CONVERSION

CRYOGENIC REMOTE SENSING PHYSIOGRAPH

This is a continuation-in-part of our co-pending application Ser. No. 871,925 filed June 9, 1986, now abandoned.

BACKGROUND OF THE INVENTION

Many physiological processes are characterized by the generation and propagation of multiple, dynamic and often transient electrical phenomena from the respective tissues and organs where they originate. The purpose of recording physiological signals is to obtain a record which is an exact facsimile of the events under investigation. However, it is seldom feasible to attach pickup elements directly to the tissues or organs being investigated, and some method of sensing the electrical phenomena from the surface of the body is usually employed. Such methods introduce measurement errors that result in a distorted picture of the processes being recorded. In spite of this limitation, these techniques have proven to be highly useful for the medical profession.

A wide variety of pickup elements of various sophistication have been developed and are presently available for recording many important phenomena associated with various physiological function from different anatomical sites. The important requirements for sensing electrodes and transducers presently employed in electrophysiological monitoring and recording are: (a) attachment to the body must result in a minimum of discomfort and movement restriction; (b) once applied, they should maintain their operation status without deterioration for extended periods of time; (c) avoid the necessity for reapplication and/or relocation; and (d) they must allow for a far greater degree of subject movement than usually prevails in clinical investigations.

Although a great deal of effort has already been spent in reducing the weight and size of electrodes and transducers, and in minimizing the adverse effects that occur over prolonged time periods, the present state of the art is far from ideal.

The methods employed for applying even simple bioelectric pickup electrodes in many instances is quite traumatic, as they require abrasion and debridement of the superficial keratinized skin layers. Such procedures frequently cause discomfort, and many contribute to the cause of skin reactions when electrodes are left applied to the same locations for many hours or days. The following scientific studies published in scientific and medical Journals are indicative of previous efforts in remotely recording electromagnetic fields that correspond to internal physiological processes of biological organisms without the use of any intermediary materials or electrodes attached to the skin:

(1) Burr, H. S., and Northrop, F., "The Electrodynamic Theory of Life", *Quarterly Review of Biol.*, 1935, 10:322

(2) Burr, H. S., and Northrop, F., "Evidence For The Existence Of An Electrodynamic Field In Living Organisms", *National Academy of Sciences*, 1939, 25:284

(3) Burr, H. S., and Maure, A., "Electrostatic Fields of Sciatic Nerve In The Frog", *Yale J. of Bio. Med.*, 1949, 21:455

(4) Seipell, H., and Morrow, R., "The Magnetic Field Accompanying Neuronal Activity Of The Nervous System", *J. Wash. Acad. Sci.*, 1960, 50:1

(5) Cohen, D., "Magnetoencephalography: Evidence Of Magnetic Fields Produced By Alpha-Rhythm Currents", *Science*, 1968, 161:784

(6) Cohen, D., "Magnetoencephalography: Detection Of Brain's Electrical Activity With A Superconducting Magnetometer", *Science*, 1972, 175:664

(7) Cohen, D., "Magnetic Fields Of The Human Body", *Physics Today*, Aug. 1975, pp. 34–43

(8) Gulyaev, P. I., Zabotin, V. L. & Shippenbakh, N.Y., "The Electroauragram Of The Frog's Nerve, Muscle, Heart And Of The Human Heart And Musculature", *Doklady Biological Science*, 1968, 180, pp. 359–361

(9) Gulyaev, P. I., "The Electroauragram: The Electric Field Of Organisms As A New Biological Connection", *Proceedings Of Symposium On Physics And Biology*, Moscow, 1967, p. 19

(10) Goodman, D. A. and Weinberger, N. M., "Remote Sensing Of Behavior In Aquatic Amphibia Especially In Necturus Maculosus, The Mud Puppy", *Comm. Behavioral Biology*, 1971, 6, pp. 67–70

(11) Goodman, D. A. and Weinberger, N. M., "Submerged Electrodes In An Aquarium: Validation Of A Technique For Remote Sensing Of Behavior", *Behav. Res. Meth. & Instru.*, 1971 3:6, pp. 281–286

Other devices have eliminated the necessity of topically connecting electromagnetic sensors to a person's skin. Some of these devices are described in U. S. Pat. Nos. 3,980,076 (Wikswo et al), 4,079,730 (Wikswo et al) and 4,444,199 (Shafer). However, these devices are not totally remote in that they will not operate through the ambient atmosphere from up to 12 feet away. Similarly, there have been problems in measuring the EKG, EEG, EMG, EOG and respiration in the super-low frequency (SLF) and extremely-low frequency (ELF) range of 0.3 to 40 Hertz. Thus, there exists a need for the development of physiological monitoring methods and equipment that do not require direct contact with the subject's integument (skin layer), and thus relieve the subjects from annoyance and encumbrance of bodily attachments.

SUMMARY OF THE INVENTION

The invention comprises a method and apparatus (or system) for the investigation of electromagnetic (EM) waves in the 0.3 to 40 Hertz realm. The SLF/ELF frequency range is generally considered to be from D. C. to approximately 100 Hz. As used herein, superlow frequency (SLF) and extremely-low Frequency (ELF) is a frequency from 0.3 to 40 Hz that corresponds to internal physiological processes. The elements necessary for this type of system are: an antenna, an analog signal conditioner, fiber-optic data links, and a digital signal processor. In the preferred embodiment of the invention the antenna consists of a three element array of supercooled super-conducting niobium plates for the detection of electromagnetic waves in the 0.3 to 40 Hz range with amplitudes in the nanovolt to millivolt range. The three element antenna array is for spatial signal referencing. Each antenna element has its own integral field effective transistor (FET), pre-amplifier and filter which are enclosed in a separate, thermally regulated (via power transistor and thermostat) Dewar flask arrangements at 77° C. Kelvin as opposed to the niobium antenna plate elements which are cooled to 3.7° K. The arrayed antenna is capable of detecting SLF/ELF signals at distances of up to 12 feet. The arrayed antenna output is coupled to the input of low noise, optically isolated analog signal conditioner circuitry with self-contained power source incorporating a follower circuit and output amplifier. The analog signal circuitry has optically isolated (low-noise) first stage which reduces the random 1/f noise of the transistor which in turn improves the signal-to-noise ratio.

The next stage of the analog signal conditioner is an analog fiber-optic data link flowing into a low-pass 40 Hz filter which serves as an output buffer. The output of the signal conditioner is coupled to the input of the digital signal processor system. The input of the digital signal processor is a very fast (nanosecond) 16-bit analog-to-digital converter which allows for the storage of waveforms in the computer memory. The computer (such as a Micro Vax II by Digital Equipment Corporation) then uses a 4-port memory having serial in-time sequencing with overlapping memory windows flowing into four hard-board Fast Fourier Transform (FFT) microprocessors and four autocorrelators which are outboard, dedicated microprocessors. These FFT s and autocorrelators are coupled to a 32-bit mini computer with an array processor incorporating signal discriminating software (Micro Vax II software by Digital Equipment Corporation). The computer uses the FFT and autocorrelation analysis to examine the time dependence of amplitude and frequency modulation in the frequency range of 0.3 to 40 Hz. The FFTs and autocorrelators separate the SLF/ELF fields emitted by the human subject into component waveforms as they are related to specific internal organ functioning such as Electrocardiogram (EKG), Electroencephalogram (EEG), Electromyogram (EMG), Electrooculogram (EOG) and respiration. After the FFT, autocorrelation and signal discrimination functions are completed, the signal is sent directly to a multi-channel waveform display (color video display terminal) or physioscope, as well as being sent through a series of multi-channel digital-to-analog converters (very fast) that lead to a chart recorder or electrostatic printer which records the various component waveforms on a chart.

It is an object of the present invention to provide an improved method and apparatus or system for monitoring physiological changes in a human subject without attaching electrodes and/or sensors or other devices to the subject's body.

Another object of the present invention is to permit the unshielded remote monitoring of a human subject at a distance of up to 12 feet.

Still another object of the invention is to provide a system that is substantially insensitive to other electrical equipment operating in the same area and to provide a system with a high signal-to-noise ratio.

It is a further object of the invention to provide a system that has the ability to discriminate between readings of EKG, EEG, EMG, EOG and respiration.

DESCRIPTION OF THE PREFERRED EMBODIMENTS

There has long been a need for remotely monitoring basic human physiological data. The main problems in this type of biomonitoring is recognizing signals such as EKG, EEG, EMG, EOG and respiration at a point remote from the human subject being monitored and separating these various signals from background noise and other sources of interference. These super-low frequency (SLF) and extremely-low frequency (ELF) electromagnetic waves are generated and propagated by the human body in the frequency range of from about 0.3 Hz to about 40 Hz.

Figure 1:
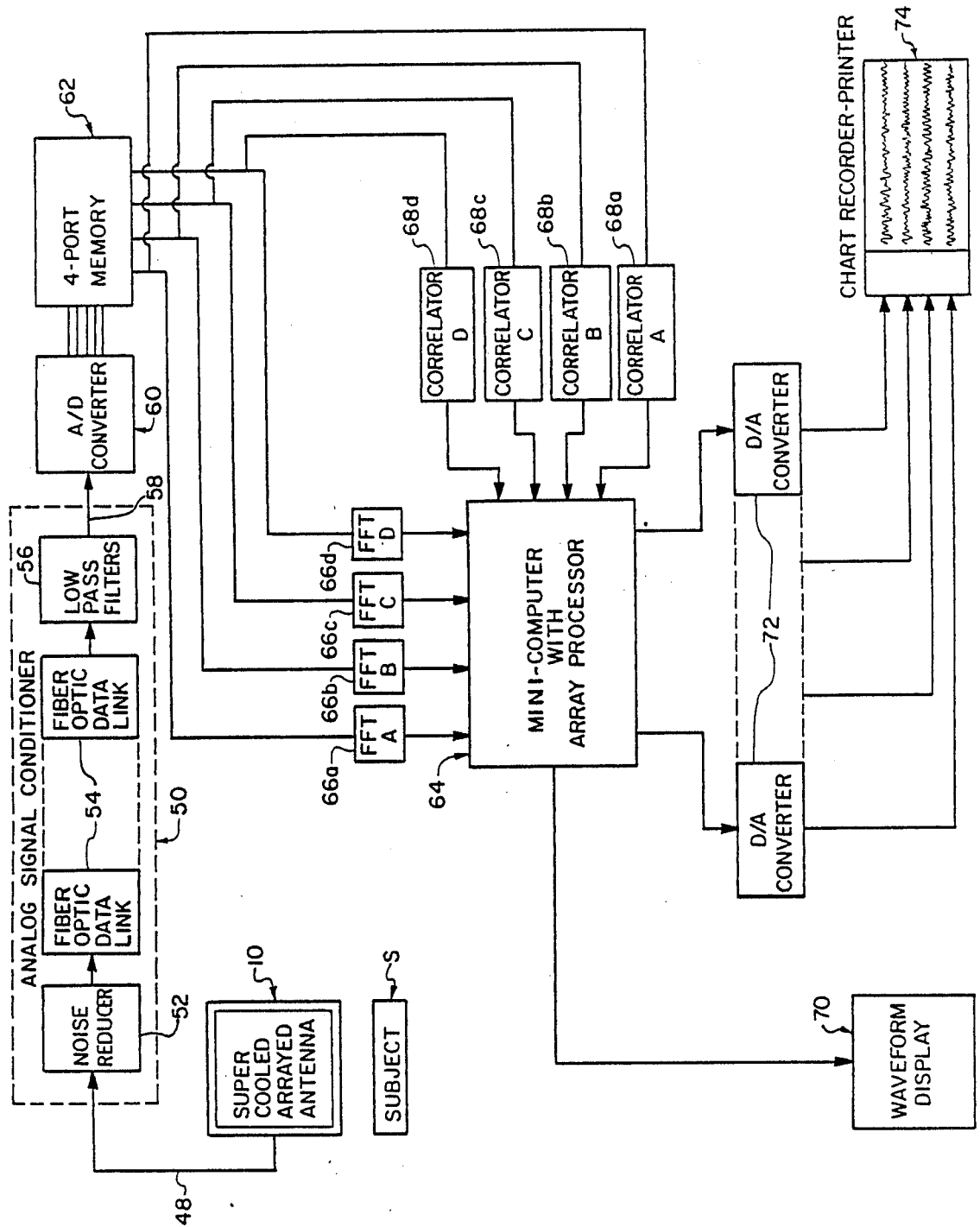
FIG. 1 is a block diagram of the cryogenic remote sensing physiograph (CRESP)system of the present invention in its preferred embodiment.
Figure 2:
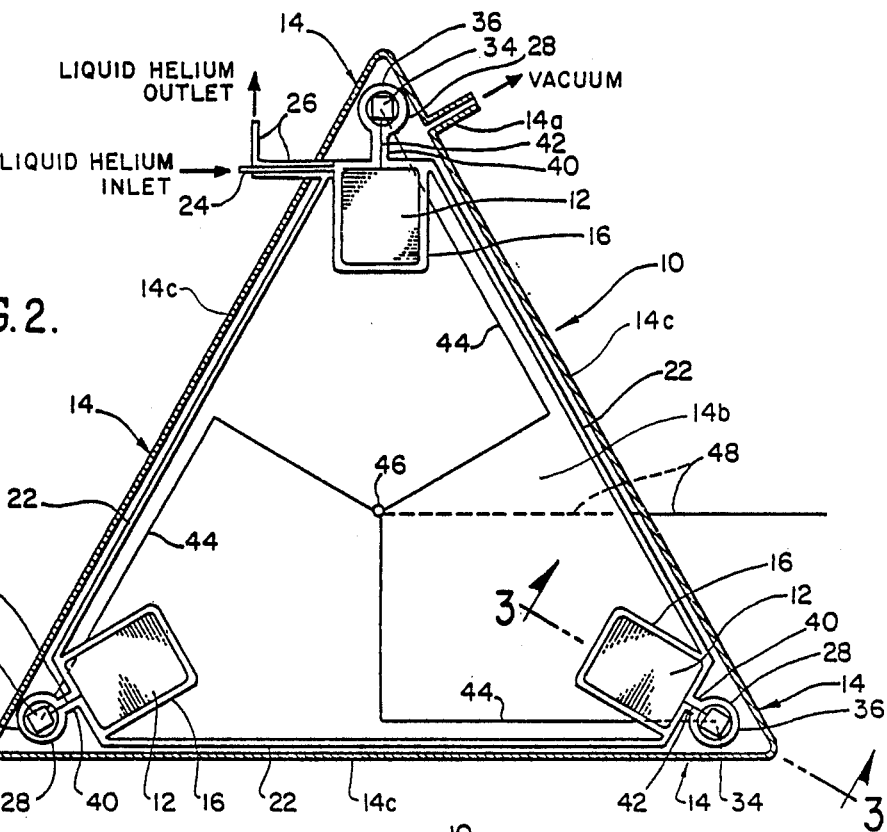
FIG. 2 is a top sectioned view of a supercooled arrayed antenna in accordance with the invention.

The cryogenic remote sensing physiograph (CRESP) system of the present invention uses three basic elements for the investigation of electromagnetic waves in the 0.3 to 40 Hz range. These elements comprise an arrayed antenna of special design, an analog signal conditioner with fiber optic data links and low pass filtering, and a digital signal processor with 4-port memory. FIG. 1 is a block diagram of the entire CRESP system. FIG. 2 is a top sectioned view of the supercooled arrayed antenna with FIG. 3 comprising a partial section view of the arrayed antenna of FIG. 2.

Figure 3:
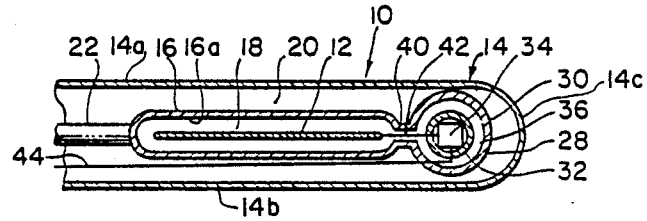
FIG. 3 is a partial section view of the antenna structure of FIG. 2 taken along line 3—3 in FIG. 2.

Referring initially to FIGS. 2 and 3, the arrayed antenna 10 of the invention consists in its primary structure of a three element array of super-conducting niobium plates 12 for the detection of electromagnetic waves in the 0.3 to 40 Hz range. The niobium plates 12 are preferrably rectangular in shape, measuring 8"×10" with a thickness of approximately 30 mils, and are arrayed within an equilateral triangular outer enclosure 14. The antenna plates 12, each located at a corner within the outer triangular enclosure 14, are also individually enclosed in an inner antenna housing 16 defining space 18 containing recirculating liquid helium. The outer enclosure 14 has parallel top and bottom walls 14a and 14b, respectively, and annular wall 14c formed of carbon-fiber composite material or polycarbonate and the inner housings 16 have walls formed of the same material. The internal surfaces 16a of the antenna housings 16 are aluminized and space 20, surrounding the antenna housings and defined by outer enclosure 14, is maintained under vacuum. The vacuum may be drawn on space 20 within enclosure 14 via outlet pipe 14a. Thus, each antenna plate 12 is (in effect) contained in a Dewar flask type arrangement, i.e., a double-wall container that has an evacuated space (space 20) between its outer wall (enclosure 14) and inner wall (housing 16) with its innermost surfaces 16a bearing a reflective coating to inhibit heat transfer between the liquid helium in space 18 and the ambient atmosphere surrounding the arrayed antenna enclosure 14.

The three antenna housings 16 are interconnected by pipe sections 22 of carbon-fiber composite or polycarbonate material having internally aluminized surfaces. These pipe sections assist in supporting and positioning the antenna plate housings 16 within the triangular enclosure 14 and provide means for circulating liquid helium throughout the antenna system. Liquid helium may be introduced to such system by inlet pipe 24 and withdrawn from the system by outlet pipe 26.

To the rear of each antenna plate housing 16 is a separate Dewar arrangement 28 consisting of an outer spherical housing 30 and a spaced inner spherical encasement 32 within which is contained the individual array element analog circuitry package 34 including a field effect transistor (FET), preamplifier, filter and D. C. power supply. Each array element package 34 incorporates its own low-noise, optically isolated analog source-following circuitry and an output amplifier. The space 36 between spherical housing 30 and spherical encasement 32 of each Dewar arrangement 28 is interconnected to the space 18 of its associated antenna housing 16 by a pipe section 40 so that liquid helium is circulated within space 36.

From the foregoing description of the arrayed antenna 10 of the invention, it will be noted that each antenna plate 12 and each associated circuitry package 34 is encased in a supercooled environment. Circulation of liquid helium throughout the antenna structure may be accomplished by a closed-cycle, unvented, nonconsumable, recirculating system (not shown in FIG. 2) such as the "Heliplex" System produced by Air Products and Chemicals, Inc. Through appropriate control of the helium recirculating system the temperature of the niobium antenna plates 12 may be maintained at a desired operating temperature of approximately 3.7° Kelvin. Each of the Dewar arrangements 28 (encompasing the circuitry packages 34) are thermally regulated to a temperature of about 77° K. through the use of a power transistor and thermostat powered by an internal D. C. power supply to avoid any coupling with stray A. C. power fields. The antenna leads 42 and output leads 44 from each of the Dewar-encased circuitry packages 34 are composed of niobium-tin alloy to further reduce system noise. The leads 44 exit the outer enclosure 14 at a central point 46 and connect to the analog signal conditioner of the CRESP system of the invention through cable 48.

Referring now to FIG. 1, the previously described supercooled arrayed antenna is represented by box 10 and is shown in the proximity of a human subject represented by box S. The antenna, in accordance with the invention may be placed at a distance of up to twelve feet from the subject with no contact with, or connection made to, the subject. The antenna cable 48, comprising the antenna array output leads 44, is coupled to the analog signal conditioner section 50 of the CRESP system. The optically isolated (low-noise) first stage 52 of signal conditioner 50 reduces the random 1/f noise of the antenna transistors and improves the signal-to-noise ratio of the system. The antenna signals are next passed to the fiber optic data link stage 54 of the conditioner 50 and thence into a low-pass filter stage 56. The low-pass filters are required to eliminate noise and frequencies over 40 Hz. It is especially important that these filters are tuned to null at 60 Hz. Further, the filters must be designed for sufficient stability and high Q to assure that successive stages will not be saturated by a 60 Hz power field. The 60 Hz power fields are typically generated by A. C. power lines within walls, overhead lighting systems, and various electro-mechanical apparatus in the immediate proximity of the CRESP system as part of the normal environment within which the system will be operated.

The output 58 of the low-pass filter stage 56 is connected to a very fast (nanosecond), 16-bit analog-to-digital converter 60 which converts the analog information to digital information so that it can be stored in the 4-port memory section 62 of a minicomputer 64. The 4-port memory section 62 has serial, in time sequencing with overlapping memory windows. This 4-port memory flows into four hard-board Fast Fourier Transform- (FFTs A to D) dedicated outboard microprocessors 66a–66d and four outboard dedicated autocorrelator microprocessors (correlators A to D) 68a–68d. The FFT and autocorrelator microprocessors are coupled to the minicomputer 64 (32-bit) with an array processor and incorporating signal discriminating software such as the previously mentioned Micro Vax II software by Digital Equipment Corporation. The minicomputer 64 uses the FFT and autocorrelation analysis to examine the time dependence of amplitude and frequency modulation for frequencies in the range of 0.3 Hz to 40 Hz. Explanations of how this analysis may be accomplished are contained in the following references:

(1) Cochran, W. T., "What is the Fast Fourier Transform?", *IEEE Transactions on Audio and Electroacoustics*, Vol AU-15, No. 2, June 1967

(2) Brigham, O. E., *The Fast Fourier Transform*, Prentice-Hall, Englewood Cliffs, N.J., 1974

(3) Raeder, W. A., *The Fast Fourier Transform: A Bibliography*, TRW Systems, Redondo Beach, Calif. 1969

(4) Luk, A. L., *Parallel Processing of the Fast Fourier Transform Via Memory Organization*, M.S. Thesis in Computer Science, UCLA, 1976

The FFTs 66a–66d and autocorrelators 68a–68d separate the SLF/ELF fields emitted by the human subject S into component waveforms as they are related to specific internal organ functioning such as EKG, EEG, EMG, EOG and respiration. After the FFT, autocorrelation and signal discrimination functions are completed by the minicomputer 64, the signal is sent directly to a multichannel waveform display unit 70 (color video display terminal) or physioscope, as well as being sent through a series of multichannel digital-to-analog (very fast) converters 72 that pass their output to a chart recorder or electrostatic printer 74 which records the various component waveforms on a chart.

Figure 4:
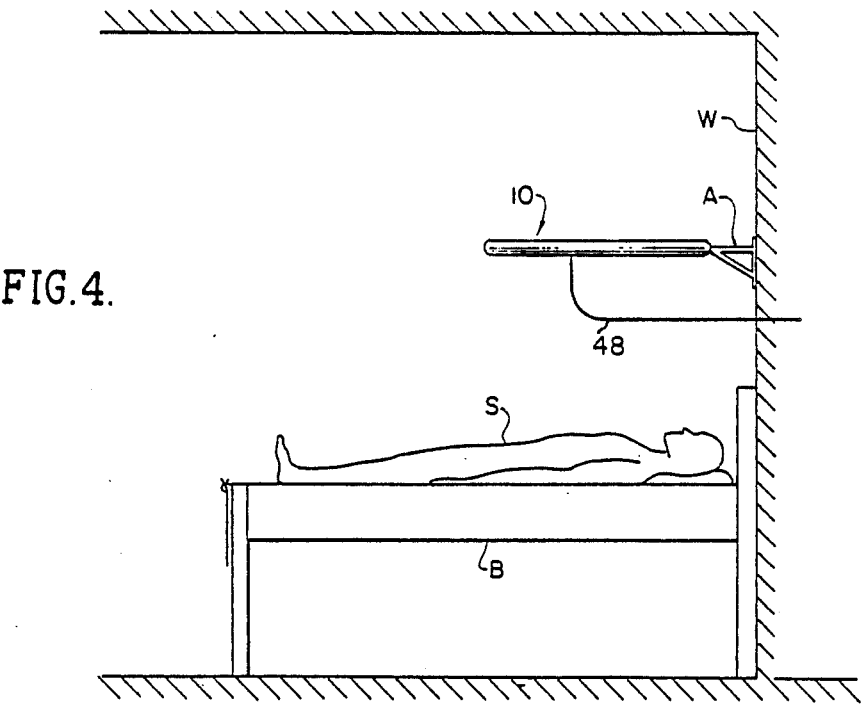
FIG. 4 is a schematic representation of a human subject.being remotely monitored by the antenna of FIG. 2.

FIG. 4 shows a patient or subject S being monitored by the arrayed antanna structure 10 of the invention. The antenna is attached to a wall W of an examination room by support arms A. The antenna output signals are passed to the analog signal conditioner section of the CRESP system through cable 48. The triangular antenna structure is positioned parallel to the subject S and aligned so that one of the antenna plate elements is directly over the head and chest area of the subject. The remaining two array plate elements are positioned over the lower torso area of the subject. The antenna 10 may be attached to the structure of the bed B or a wheeled cart containing the CRESP system.

The following comprises a discussion of the factors determining the selection and design of an appropriate antenna for the remote monitoring of 0.3 to 40 Hz electromagnetic waves. Wavelengths of frequencies in the 0.3 Hz to 40 Hz range are extremely long, $1 \times 10^9$ meters to $7.5 \times 10^6$ meters, respectively, and the distance between any system involving a transmitter (a human body) and a receiver (the system of the present invention) will be considerably less than the wavelengths of the signals being measured. Thus, the super-low frequency (SLF) and extremely-low frequency (ELF) signals and their concomitant long wavelengths demand novel approaches when the antenna is placed at a distance anywhere from two to twelve feet away from the transmitter, i.e., the human subject being monitored.

Due to the superlong wavelengths, the classical approach to antenna theory does not hold. Under such circumstances, the antenna problem is reduced to a matter of electrostatics. Examination of the various conditions shows that the antenna problem may be resolved into three basic cases. In case 1 the transmitter is distant from a large ground plane and the receiver is near the large ground plane. In the second case, the transmitter and receiver are in free space. In the third case, both the transmitter and receiver are located near one another and both are in the presence of a large ground plane.

For the first case above, the theoretically best antenna is the largest possible section of the ground plane which is insulated from the rest of the ground plane. This because the electric field is perpendicular to the plane. The sensitivity is in proportion to the size of the plane antenna. For the second case above, there must be an electric dipole formed for reception. In this case, the optimum antenna is the largest possible parallel plane capacitor, with the best sensitivity in the vector which is perpendicular to the plane of the antenna. For the third case above, the receiver should be connected to a common ground plane. The antenna is a large conductive sheet oriented perpendicular to the subject being monitored.

The foregoing antenna problems and needs for accomplishing the remote monitoring of basic physiological data are solved by the unique arrayed antenna structure of the present invention integrated into the CRESP system as described hereinbefore.

Figure 5:
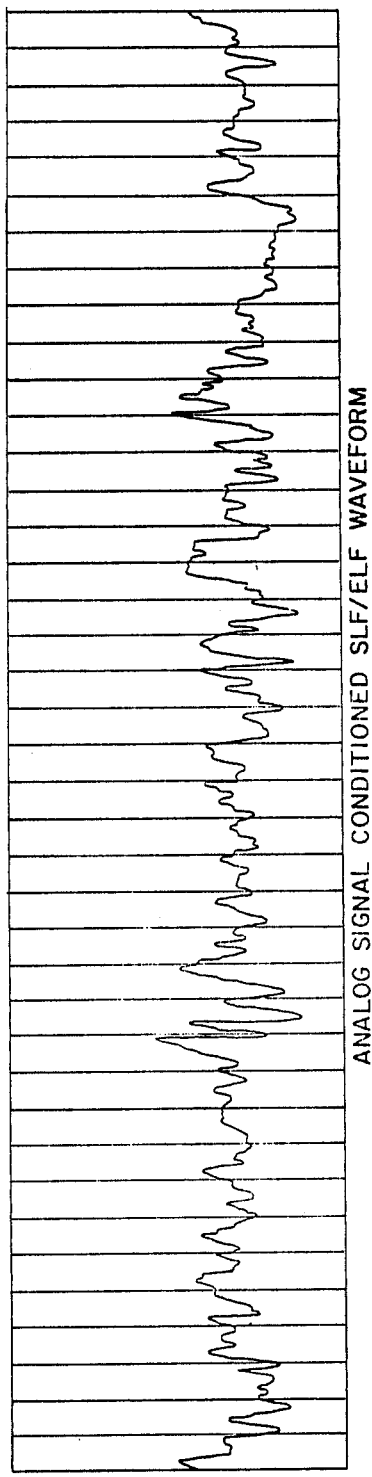
FIG. 5 shows a waveform after it has been processed by the analog signal conditioner of the CRESP system.
Figure 6:
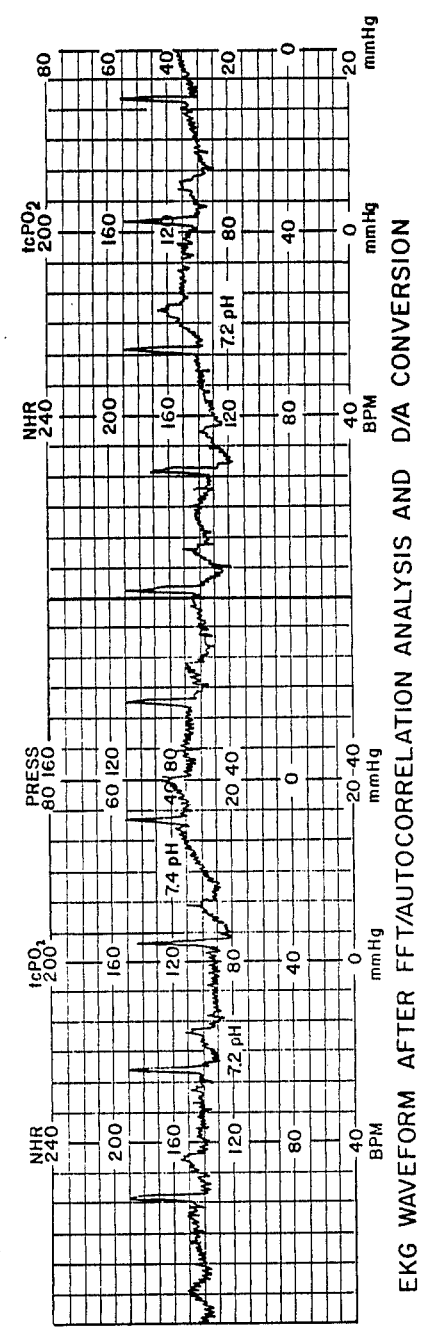
FIG. 6 shows an EKG signal after FFT/autocorrelation analysis and D/A conversion by the CRESP system.
Figure 7:
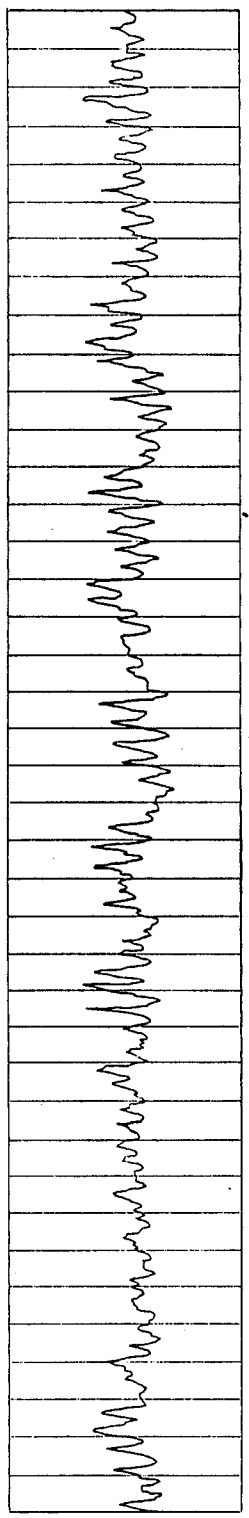
FIG. 7 shows an EEG signal after FFT/autocorrelation analysis and D/A conversion by the CRESP system.
Figure 8:
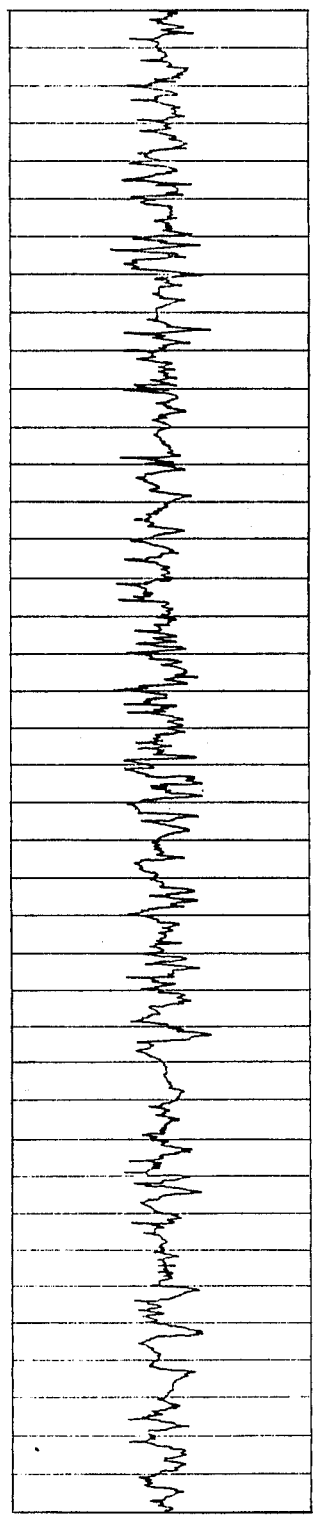
FIG. 8 shows another EEG signal after FFT/autocorrelation analysis and D/A conversion by the system.
Figure 9:
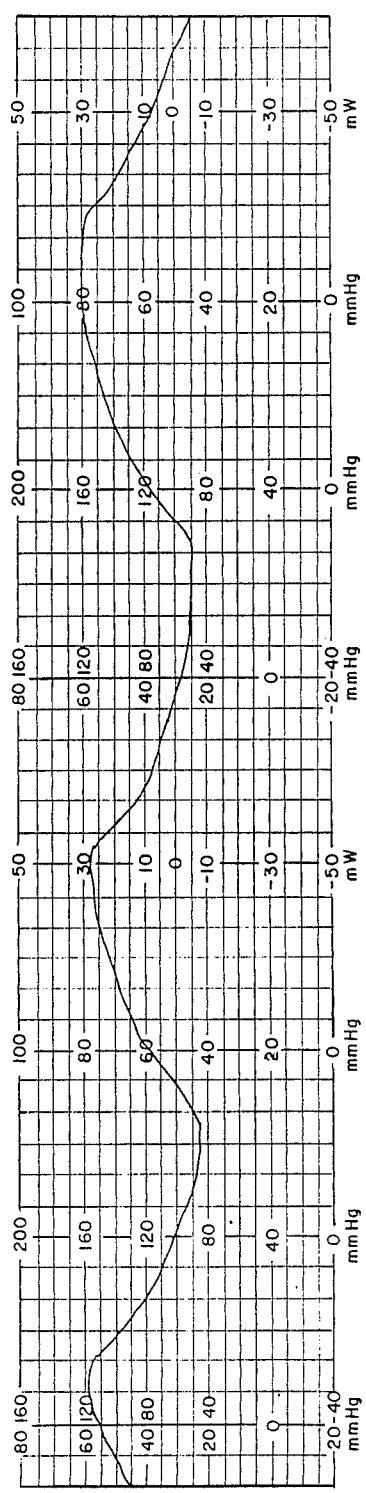
FIG. 9 shows a respiration signal after FFT/autocorrelation analysis and D/A conversion by the CRESP system of the invention.

The output of the antenna array analog signal conditioners of the CRESP system consists of a complex waveform emanated from the human body. This complex waveform is composed of various wavelengths and amplitudes which correspond to internal physiological processes and a typical waveform, as actually processed by the apparatus and methodology of the invention, is shown in FIG. 5. The computer FFT/autocorrelation analysis separates this complex waveform into its various frequency/amplitude components as they are related to the specific internal organ functioning. FIGS. 6, 7, 8 and 9 show typical EKG, EEG and respiration waveforms, respectively, as actually generated by the apparatus and methodology of the invention, after FFT/autocorrelation analysis and D/A convesion. EMG and EOG waveforms have not been shown.

While a preferred embodiment of the present invention has been illustrated and described, modifications and variations thereof will be apparent to those skilled in the art given the teachings herein, and it is intended that all such modifications and variations be encompased within the scope of the appended claims.

What is claimed is:

1. Apparatus for remotely monitoring the internal physiological processes of a human subject by measuring the electromagnetic signals emanating from the body of said subject and separating said signals into EKG, EEG, EMG, EOG and respiration waveform representing said physiological processes, comprising:
   (a) an arrayed antenna adapted to be located in a spaced remote relationship of up to about 12 feet from the body of a human subject, the arrayed antenna including three like supercooled superconducting metallic antenna plates for detecting electromagnetic signals in the 0.3 to 40 Hertz frequency range emanating from the physiological processes of said subject, said the arrayed antenna having three like supercooled analog circuitry packages each interconnected to one of said metallic plates for outputting said electromagnetic signals;
   (b) an analog signal conductor having an input stage coupled to the analog circuitry packages of the arrayed antenna and including means adapted to receive and improve the signal-to-noise ratio of the detected electromagnetic signals and said signal conditioner having an output stage including a low-pass filter for filtering out signal frequencies of over 40 Hertz from said electromagnetic signals;
   (c) an analog-to-digital converter coupled to the output stage of the analog signal conditioner to receive and convert the 0.3 to 40 Hertz electromagnetic signals to digital signals;
   (d) a digital signal processor means coupled to the analog-to-digital converter to receive and separate said digital signals into component waveforms representing the internal physiological processes of said human subject, said digital signal processor means comprising a minicomputer including 4-port memory with serial in-time sequence overlapping memory windows and dedicated outboard Fast Fourier Transform and autocorrelator microprocessors coupled to said minicomputer with signal discriminating software for directing the separation of said digital signals by said minicomputer into component waveforms representing the physiological processes of said subject; and
   (e) means coupled to said digital signal processor means for displaying and permanently recording said component waveforms.

2. Apparatus for remotely monitoring the internal physiological processes of a human subject as claimed in claim 1 wherein the metallic antenna plates of said arrayed antenna are niobium sheet elements and are arranged in equilateral triangular relationship with one another for spatial signal referencing.

3. Apparatus for remotely monitoring the internal physiological processes of a human subject as claimed in claim 1 wherein the metallic antenna plates of said arrayed antenna are encased in liquid helium and thereby supercooled to about 3.7° Kelvin.

4. Apparatus for remotely monitoring the internal physiological processes of a human subject as claimed in claim 1 wherein the arrayed antenna, including said three like metallic antenna plates and said three like analog circuitry packages, is encased within an equilateral triangular outer enclosure with each of said antenna plates located at a corner of said outer enclosure and being individually encased in a sealed inner enclosure in a liquid helium environment, said inner enclosure for said antenna plates being spaced from said outer enclosure with the space between said outer enclosure and said inner enclosures being in communication with means to maintain said space under vacuum.

5. Apparatus for remotely monitoring the internal physiological processes of a human subject as claimed in claim 4 wherein the supercooled three like analog circuitry packages each include a field effect transistor, a preamplifier, a filer and a D.C. power supply, and each of said circuitry packages are contained in a Dewar in a liquid helium environment to maintain said circuitry packages at a temperature of about 77° Kelvin with each Dewar containing a circuitry package located in close proximity to one of the inner enclosure encasing said metallic antenna plates within the equilateral triangular outer enclosure of said arrayed antenna.

6. A method for remotely monitoring the internal physiological processes of a human subject by measuring the electromagnetic signals emanating from the body of said subject and separating said signals into EKG, EEG, EMG, EOG and respiration waveforms representing said physiological processes, comprising:
 (a) positioning a supercooled multi-plate arrayed antenna, including supercooled analog circuitry packages associated with the plates thereof, in a spaced remote relationship of up to about 12 feet from the body of a human subject for detecting electromagnetic signals in the 0.3 to 40 Hertz frequency range emanating from the physiological processes of said subject;
 (b) passing the electromagnetic signals detected by said antenna from the output of said antenna to a noise reduction input stage of an analog signal conditioner for improving the signal-to-noise ratio of the detected electromagnetic signals and thereafter through a low-pass filter output stage of the analog signal conditioner to filter out from the detected electromagnetic signals those signal frequencies over 40 Hertz;
 (c) passing the 0.3 to 40 Hertz electromagnetic signals from the output stage of the analog signal conditioner through an analog-to-digital converter to convert the 0.3 to 40 Hertz electromagnetic signals to digital signals;
 (d) passing the digital signals of the analog-to-digital converter through a digital signal processor for separating the digital signals into component waveforms representing the internal physiological processes of said subject and
 (e) transmitting said component waveforms to means for display their and permanent recordation.

7. A method for remotely monitoring the internal physiological processes of a human subject as claimed in claim 6 wherein liquid helium is circulated over the plates of the supercooled multi-plate arrayed antenna to maintain said plates at a temperature of approximately 3.7° Kelvin.

8. A method for remotely monitoring the internal physiological processes of a human subject as claimed in claim 6 wherein Fast Fourier Transform and autocorrelation signal analyses are performed by the digital signal processor for separating said digital signals into waveforms corresponding to the internal physiological processes of said subject.

9. A method for remotely monitoring the internal physiological processes of a human subject as claimed in claim 8 wherein the plates of said antenna are maintained at a temperature of about 3.7° Kelvin and the analog circuitry packages of said antenna are maintained at a temperature of about 77° Kelvin.

* * * * *